United States Patent [19]

Sato et al.

[11] Patent Number: 4,717,770

[45] Date of Patent: Jan. 5, 1988

[54] PROCESS FOR PRODUCING EPSILON-CAPROLACTAM

[75] Inventors: Hiroshi Sato; Kenichi Hirose; Masaru Kitamura, all of Osaka; Hideto Tojima; Norio Ishii, both of Kyoto, all of Japan

[73] Assignee: Sumitomo Chemical Co., Ltd., Osaka, Japan

[21] Appl. No.: 19,921

[22] Filed: Feb. 27, 1987

[30] Foreign Application Priority Data

Feb. 27, 1986 [JP] Japan .................. 61-43441

[51] Int. Cl.$^4$ .......................................... C07D 201/04
[52] U.S. Cl. .................................... 540/536; 540/535
[58] Field of Search ........................... 540/535, 536

[56] References Cited

U.S. PATENT DOCUMENTS

| 4,046,859 | 9/1977 | Plank et al. ............... 423/328 |
| 4,061,724 | 12/1977 | Grose et al. .............. 423/335 |
| 4,359,421 | 11/1982 | Bell ........................ 540/535 |
| 4,472,516 | 9/1984 | Frenken ..................... 502/60 |

FOREIGN PATENT DOCUMENTS

| 2830787 | 1/1980 | Fed. Rep. of Germany ...... 540/535 |
| 3006471 | 8/1981 | Fed. Rep. of Germany ...... 540/535 |
| 46-12125 | 3/1971 | Japan ...................... 540/536 |
| 46-10064 | 3/1971 | Japan ...................... 585/467 |
| 50-149900 | 6/1975 | Japan ...................... 585/467 |
| 52-144500 | 4/1977 | Japan ...................... 585/467 |
| 52-16079 | 6/1977 | Japan ...................... 585/467 |
| 53-37686 | 3/1978 | Japan ...................... 540/536 |
| 53-23280 | 7/1978 | Japan ...................... 585/467 |
| 56-133223 | 9/1981 | Japan ...................... 585/467 |
| 57-139062 | 7/1982 | Japan ...................... 540/536 |
| 57-149819 | 9/1982 | Japan ...................... 540/536 |
| 59-164617 | 9/1984 | Japan ...................... 585/467 |
| 881927 | 11/1961 | United Kingdom ............ 540/535 |

OTHER PUBLICATIONS

J. Chem. Soc. of Japan No. 1, pp. 77–81 (1977).
J. Catalysis 6, pp. 245–252 (1966).
Catal. Rev. Sci. Eng. 27(3), pp. 461–514 (1985).
7th Seminar, Catalyst Soc. (1984).
8th Seminar, Catalyst Soc. (1985).
10th Seminar, Catalyst Soc. (1986).
29 Dokl. Akad. Nauk BSSR No. 10, 924–927 (1985).

Primary Examiner—Robert T. Bond
Attorney, Agent, or Firm—Cushman, Darby & Cushman

[57] ABSTRACT $\epsilon$-caprolactam is prepared by gas phase catalytic synthesis where cyclohexanone oxime is brought into contact with a crystalline zeolite, for example, aluminosilicate zeolite or metallosilicate zeolite having a constraint index of 1–12 which has been surface treated with an organometallic compound represented by the general formula: $R_{4-n}MX_n$ wherein R which may be identical or different represent an alkyl group of 1–6 carbon atoms or phenyl group, M represnets Si or Ge, X represents Cl or an alkoxy group of 1–6 carbon atoms and n represents 1 or 2.

9 Claims, No Drawings

PROCESS FOR PRODUCING EPSILON-CAPROLACTAM

BACKGROUND OF THE INVENTION

This invention relates to a process for producing ε-caprolactam and more particularly, to a process for producing ε-caprolactam from cyclohexanone oxime wherein a crystalline zeolite catalyst subjected to a surface treatment with a specific chemical agent is used.

ε-caprolactam is an important raw material for nylon and the like. One of the processes for preparing the caprolactam is liquid phase rearrangement of cyclohexanone oxime using sulfuric acid as a catalyst.

Furthermore, there have been proposed various processes of gas-phase rearrangement using a solid acid as a catalyst. For example, there has been proposed use of boric acid catalyst (Japanese Published Unexamined Patent Application Nos. 37686/78 and 12125/71), silica alumina catalysts (British Pat. No. 881927), solid phosphoric acid catalysts, mixed metal oxide catalysts (Journal of the Chemical Society of Japan, No. 1, 77, 1977), zeolite catalysts (Journal of Catalysis, 6, 247, 1966) and crystalline alumino-silicate catalysts (Japanese Published Unexamined Patent Application No. 139062/82) or the like.

The above process of using sulfuric acid has problems such as use of a large amount of fuming sulfuric acid, by-production of a large amount of ammonium sulfate, corrosion of apparatuses with fuming sulfuric acid, etc.

For solving these problems, it has been proposed to use various solid acids as described above. However, these processes still have problems in reaction selectivity of ε-caprolactam, life of catalysts, productivity per catalyst, etc.

For example, Japanese Published Unexamined Application No. 139062/82 shows a specific example where a crystalline zeolite such as ZSM-5 having an atomic ratio Si/Al of 40-60 was used as a catalyst and states that the conversion rate of cyclohexanone oxime is quantitative, but in this case, weight hourly space velocity (referred to as "WHSV" hereinafter) was very low of about 2.5 hr$^{-1}$ and life of catalyst was very short, namely, 15-20 hours.

The present inventors have also studied use of ZSM zeolites having the Si/Al atomic ratio as mentioned in the above patent application and have found that not only the life of catalyst, but the selectivity of ε-caprolactam are not enough and especially under practical WHSV, for example, about 10 hr$^{-1}$ or higher, life of catalyst is extremely short and besides selectivity is markedly low.

Thus, use of solid acid catalysts does not simultaneously satisfy the conversion rate of oxime, selectivity of lactam and life of catalysts and further does not provide enough productivity. Therefore, further improvements have been demanded.

Under the circumstances, in an attempt to find a further improved process for production of ε-caprolactam, the present inventors have made intensive research on crystalline zeolite catalysts having a constraint index of 1-12 and as a result it has been found that when crystalline zeolite catalysts subjected to a surface treatment with a specific chemical agent, not only conversion rate of oxime and selectivity of lactam are markedly improved, but also life of catalyst is sharply prolonged and besides productivity is also improved.

SUMMARY OF THE INVENTION

That is, the present invention provides an industrially superior process for producing ε-caprolactam by contacting cyclohexanone oxime in gas-phase with a crystalline zeolite catalyst having a constraint index of 1-12, characterized by using a crystalline zeolite catalyst subjected to a surface treatment with an organometallic compound represented by the following general formula (I):

$$R_{4-n}MX_n \qquad (I)$$

(wherein R which may be same or different represent alkyl group of 1-6 carbon atoms or phenyl group, M represents Si or Ge, X represents Cl or alkoxy group of 1-6 carbon atoms and n is 1 or 2.).

The crystalline zeolites having a constraint index of 1-12 which are used in the present invention include alumino-silicate zeolites and metallosilicate zeolites exchanged with a metal atom other than aluminum in their skeleton. Typical examples of the former are "ZSM zeolite" manufactured by Mobile Oil Co. and "Silicalite" manufactured by U.C.C. and there are further included "Nu zeolite", "EU zeolite" manufactured by I.C.I., (Catalysis Reviews-Science & Engineering 27, 461, 1985), "ZSM Zeolite" manufactured by BASF (West German Pat. Nos. 2830787 (1980) and 3006471 (1981)), "TPZ Zeolite" manufactured by Teijin Yuka Co., Ltd. (Japanese Published Unexamined Application No. 149819/82).

The metallosilicate zeolites include those aluminosilicate zeolites mentioned above wherein aluminum atom in skeleton is exchanged with other metal atoms and as examples thereof, mention may be made of crystalline metallosilicate zeolites such as gallium silicate, iron silicate, cobalt silicate, boron silicate, titanium silicate, zirconium silicate, niobium silicate, bismuth silicate, zinc silicate, chromium silicate, beryllium silicate, lanthunum silicate, hafnium silicate, vanadium silicate, nickel silicate, antimony silicate, etc.

The "constraint index" used herein means degree of controlling access of molecules having larger sectional area than n-hexane by pore structure of zeolite crystal and is defined by the following formula:

$$\text{Constraint index} = \frac{\log_{10}(\text{remaining n-hexane})}{\log_{10}(\text{remaining 3-methylpentane})}$$

The method of measurement is described in Japanese Published Unexamined Application No. 133223/81. Outline is that a mixture of n-hexane and 3-methylpentane different in effective molecular diameter is allowed to contact with a zeolite catalyst under specific conditions to cause cracking reaction and the constraint index is calculated from the reactivity ratio. The values somewhat vary depending on the measuring conditions and average value is taken after measurement is made under various conditions.

As examples of crystalline zeolite having a constraint index of 1-12, mention may be made of the following crystalline aluminosilicate zeolites.

| | Constraint index | |
|---|---|---|
| ZSM-5 | 8.3 | (Japanese Published Examined Patent Application No. 10064/71) |
| ZSM-11 | 8.7 | (Japanese Published Examined Patent |

| | Constraint index | |
|---|---|---|
| | | Application No. 23280/78) |
| ZSM-12 | 2 | (Japanese Published Examined Patent Application No. 16079/77) |
| ZSM-23 | 9.1 | (Japanese Published Examined Patent Application No. 149900/76) |
| ZSM-35 | 4.5 | (Japanese Published Unexamined Patent Application No. 144500/78) |
| ZSM-38 | 2 | (U.S. Pat. No. 4,046,859) |
| ZSM-48 | 3.4 | (Japanese Published Unexamined Patent Application No. 133223/81) |
| Silicalite | 8.5 | (U.S. Pat. No. 4,061,724) |

X-ray patterns and producing processes thereof are disclosed in respective literatures.

Examples of crystalline zeolites having a constraint index of 1–12 further include crystalline metallosilicate zeolites which correspond to each of the above crystalline alumino-silicate zeolites where aluminum is replaced with other metals.

Especially preferred are ZSM-5, Silicalite and metallo-silicate zeolites having crystal structure corresponding to ZSM-5 and Silicalite.

Among crystalline zeolites having a constraint index of 1–12, those having greater Si/Al atomic ratio or Si/metal atomic ratio have higher effect of surface treatment with organometallic compounds. The Si/Al atomic ratio or Si/metal atomic ratio is preferably 200 or greater, more preferably 500 or greater.

The greater external surface area provides, the higher surface treatment effect and the external surface area is preferably at 5 m$^2$/g or more. Furthermore, less acid amount of external surface tends to provide the higher surface treatment effect.

Si/Al atomic ratio or Si/metal atomic ratio is calculated on the basis of atomic absorption spectroscopy, after high crystallinity has been confirmed, for example, by X-ray analysis by exact elemental analysis of Si and Al or metal in the crystal skeleton of zeolite. The ratio may also be calculated from $^{29}$Si signal in MAS-NMR spectrum.

The external surface area is measured by the ordinary pore-filling method which comprises filling pores in crystal of crystalline zeolite with organic or inorganic molecules and calculating the surface area by BET method from adsorption amount of nitrogen or krypton onto the external surface. The molecules to fill the pores are organic molecules such as butane, hexane, benzene, etc. or water (materials for 7th and 8th seminars on catalysts, Catalyst Society, Japan, 1984 and 1985) or organic amines and tetraalkylammonium cations used as a crystallization controlling agent in hydrothermal synthesis of zeolites. With reference to the use of latter two compounds, hydrothermal synthesis of a high-silica zeolite which is a crystalline zeolite having a constraint index of 1–12 and a greater Si/Al or Si/metal atomic ratio usually employs organic amine or tetraalkylammonium cations as crystallization controlling agent and just after the hydrothermal synthesis the crystallization controlling agent is present in the pores of the produced zeolite to fill them. Therefore, when BET surface area of the zeolite just after produced by hydrothermal synthesis and which is only sufficiently dried at 120° C. or less is measured, the value obtained corresponds to the external surface area (materials for 10th seminor on catalysts, Catalyst Society, Japan, 1986).

Crystalline zeolite catalysts having a constraint index of 1–12 may be produced by the conventional methods and those of high Si/Al atomic ratio can be produced, for example, by the methods disclosed in Japanese Published Unexamined Patent Application No. 164617/84, U.S. Pat. No. 4,061,724, "Catalyst (Shokubai)", 23 (3), 232 (1981), etc. Crystalline metallo-silicate zeolites having a higher Si/metal atomic ratio can be produced by the above methods using other metal compounds in place of Al raw materials. Furthermore those of greater external surface area can be obtained by lowering the temperature or carrying out more vigorous stirring in hydrothermal synthesis.

Zeolites obtained by hydrothermal synthesis usually contain organic amine cations as crystallization controlling agent and alkali metal cations (Na$^+$, K$^+$, etc.). Therefore, they are converted into H$^+$ form by calcining them in air to remove organic amine cations then subjecting them to ion-exchange with aqueous ammonium chloride solution or dilute aqueous hydrochloric acid solution and calcining them again or they may be converted into the corresponding polyvalent metal form by using an aqueous solution containing alkaline earth metal ions such as Ca$^{2+}$, Mg$^{2+}$, Sr$^{2+}$, Ba$^{2+}$, etc. or an aqueous solution containing lanthanoid metal ions such as La$^{3+}$, Ce$^{3+}$, etc. in place of the above aqueous ammonium chloride solution or dilute aqueous hydrochloric acid solution. Thus, zeolites may be used in these forms.

In this invention, the above mentioned zeolites which have been further subjected to surface treatment with a specific organometallic compound represented by the general formula (I) are used as catalyst.

As examples of organosilicon compounds as the organometallic compounds, mention may be made of monochlorosilanes such as chlorotrimethylsilane, chlorotriethylsilane, chlorotri-n-propylsilane, chlorotri-n-butylsilane, chlorotri-t-butylsilane, chlorotri-n-pentylsilane, chlorotri-i-amylsilane, chlorotri-n-hexylsilane, chlorophenyldimethylsilane, chlorodiphenylmethylsilane, etc.; dichlorosilanes such as dichlorodimethylsilane, dichlorodiethylsilane, dichlorodi-n-propylsilane, dichlorodi-n-butylsilane, dichlorodi-n-pentylsilane, dichlorodi-i-amylsilane, dichlorodi-n-hexylsilane, dichlorophenylmethylsilane, etc.; monoalkoxysilanes such as methoxytrimethylsilane, methoxytriethylsilane, methoxytri-n-propylsilane, methoxytri-n-butylsilane, methoxytri-n-pentylsilane, methoxytri-n-hexylsilane, methoxyphenyldimethylsilane, ethoxytrimethylsilane, ethoxytriethylsilane, ethoxytri-n-propylsilane, ethoxytri-n-butylsilane, ethoxytri-n-hexylsilane, ethoxyphenyldimethylsilane, the corresponding alkoxysilanes where the methoxy or ethoxy group above is replaced by other alkoxy group of 3–6 carbon atoms, etc; dialkoxysilanes such as dimethoxydimethylsilane; dimethoxydiethylsilane, dimethoxydi-n-propylsilane, dimethoxydi-n-butylsilane, dimethoxydi-n-hexylsilane, dimethoxyphenylmethylsilane, the corresponding silanes where the methoxy group above is replaced by other alkoxy group of 2–6 carbon atoms, etc.

Organogermanium compounds represented by the general formula (I) include those which correspond to the above organosilicone compounds where Si is replaced with Ge.

Surface treatment with these organometallic compounds may be performed by allowing a crystalline zeolite to contact with the organometallic compound in gas or liquid phase. Ordinarily, gas phase contacting is employed.

The gas-phase surface treatment may be carried out, for example, by packing a crystalline zeolite in a fixed-bed type gas-phase flow method reaction tube and passing the organometallic compound previously vaporized by a vaporizer through the zeolite. In this case, operating temperature is usually 150°–400° C., amount of the organometallic compound is usually 0.05–50 mmol, preferably 0.1–20 mmol per 1 g of the crystalline zeolite and operating time is usually several minutes—several hours although there are no special limitations. The organometallic compound may be used as such, but preferably is diluted with an inert gas such as nitrogen, helium, carbon dioxide or the like or with an inert hydrocarbon such as benzene, toluene, hexane or the like.

Further, the surface treatment of the crystalline zeolite may be effected with mixing under agitation by using a rotary reaction tube in place of the fixed-bed type reaction tube, whereby uniformity of the surface treatment can be improved.

It is presumed that in the surface treatment, silanol group on the surface of crystalline zeolite reacts with the organometallic compound and HCl or alcohol is desorbed. After completion of the surface treatment, the zeolite is well washed with a diluent gas or a solvent to remove the desorbed HCl or alcohol or unreacted organometallic compound so that they do not remain in the zeolite.

Gas phase catalytic method in a fixed-bed or fluidized bed is generally used for contacting the surface-treated crystalline zeolite catalyst with cyclohexanone oxime.

The starting material cyclohexanone oxime is vaporized in a vaporizer and is brought in the gas form into contact with the catalyst bed. In this case, cyclohexanone oxime may be fed alone, but preferably is fed as a solution in benzene or toluene to the vaporizer.

When cyclohexanone oxime diluted with benzene or toluene as mentioned above is fed and reacted, reaction carrier gas may not be used, but inert gas such as $N_2$, $CO_2$, etc. may be used as a carrier gas for reaction.

Use of carrier gas tends to improve selectivity of lactam and especially $CO_2$ gas is very high in this effect.

Catalytic rearrangement reaction temperature is usually 200°–500° C., preferably 300°–450° C. Feeding speed (WHSV) is usually 0.1–100 $hr^{-1}$, preferably 1–50 $hr^{-1}$, more preferably 5–40 $hr^{-1}$.

Isolation of ε-caprolactam is effected, for example, by cooling and condensing a reaction mixture gas and distilling or recrystallizing to separate it from unreacted starting material.

ε-caprolactam is thus produced. According to this invention, not only conversion rate of cyclohexanone oxime is improved, but also selectivity of ε-caprolactam is markedly improved, deposition of carbon on the catalyst is little, life of the catalyst is extremely prolonged and ε-caprolactam can be obtained in high yields for a long period of time.

This invention provides the advantages that the higher WHSV can be employed and productivity per catalyst can be markedly improved.

The following nonlimiting examples further illustrate this invention.

CATALYST PREPARATION EXAMPLE 1

(1-1) Synthesis of H.ZSM-5

In a 1.5 l stainless steel autoclave were charged 100 g of tetraethylorthosilicate ($Si(OEt)_4$, Al<10 ppm), 224 g of 10% aqueous solution of tetra-n-propylammonium hydroxide and 60 g of ethanol, followed by well stirring. To this mixed solution was added 48 g of previously prepared aqueous aluminum sulfate solution [$Al_2(SO_4)_3.16H_2O$ 98 mg/water 48 g], followed by vigorous stirring for 30 minutes. PH of the mixed solution was 13.0. The autoclave was tightly sealed and then dipped in an oil bath to keep the internal temperature at 105° C. Hydrothermal synthesis was effected for 120 hours with stirring by revolution of at least 400 r.p.m. Pressure within the autoclave reached 3 $Kg/cm^2$ from 2 $Kg/cm^2$. PH at the completion of the hydrothermal synthesis was 11.8. Then, a white solid product was filtered off and washed continuously with distilled water until pH of filtrate reached about 7. This product was dried at 120° C. for 16 hours. BET surface area of the crystal at this stage was measured by nitrogen gas adsorption method to obtain 10.3 $m^2/g$ of external surface area.

This dried crystal was further calcined in air stream at 500°–530° C. for 4 hours to obtain 27 g of a powdery white crystal. This was identified to be ZSM-5 by powder X-ray diffraction thereof. Si/Al atomic ratio was 1,600 according to atomic absorption spectroscopy assay.

To 10 g of this crystal was added 100 g of 5% aqueous $NH_4Cl$ solution to carry out ion exchange treatment at 50°–60° C. for one hour and then the crystal was filtered off. This ion exchange treatment was effected four times and then the crystal was washed with distilled water until no $Cl^-$ was detected and subsequently dried at 120° C. for 16 hours. Thus obtained crystal of $NH_4$ form was shaped to particles of 24–48 meshes and then calcined at 500° C. for 4 hours to obtain ZSM-5 of H-form. This H.ZSM-5 had a surface acidity of pKa= −3 measured by indicator method. Furthermore, absorption amount of 4-methylquinoline (referred to as "4MQ" hereinafter) at 350° C. was 3.92 μeq./g.

(1-2) Surface treatment with chlorotrimethylsilane

In a quartz glass reaction tube of 32 cm in length and 1 cm in inner diameter was packed 1.0 g of H.ZSM-5 catalyst of 24–48 meshes prepared in Catalyst Preparation Example 1-1 and was preheated in $N_2$ stream at 350° C. for one hour. Then, chlorotrimethylsilane (referred to as "TMCS" hereinafter) was fed by a microfeeder at a rate of 0.6 ml/hr with being diluted with and carried by $N_2$ gas (1 l/hr) at the entrance of the reaction tube. The surface treatment reaction was carried out for 4 hours with keeping the temperature of catalyst bed at 350° C. Then, feeding of TMCS was discontinued and $N_2$ gas was flowed through the tube for 15 minutes to wash the catalyst. Surface acidity of thus surface treated H.ZSM-5 was pKa= −3.0 measured by indicator method. Amount of acid on external surface was 1.84 μeq./g measured on the basis of adsorption amount of 4MQ at 350° C.

EXAMPLE 1

(A test on activity of catalyst in gas phase reaction using fixed-bed)

0.6 g (1.02 ml) of the TMCS treated H.ZSM-5 catalyst of 24–48 meshes prepared in Catalyst Preparation Example 1-2 was packed in a quartz glass reaction tube of 32 cm in length and 1 cm in inner diameter and was preheated in $N_2$ stream at 350° C. for one hour. Then, thereto was fed 8.0 wt% cyclohexanone oxime/benzene solution at a WHSV of 11.7 $hr^{-1}$ through a vaporizer and $CO_2$ gas at a rate of 0.6 l/hr to carry out reaction. Molar ratio of oxime/$CO_2$/benzene was 1/5.6/18.3 and temperature of catalyst bed (reaction temperature) was 350° C.

The reaction product was trapped and collected under water cooling and was analyzed by gas chromatography [column: 20% silicone SE-30/chromosorb AW-DMCS (60/80M) 2 m: glass column, internal standard: pseudocumene]. The results are shown in Table 1.

TABLE 1

| Time lapsed (hrs) | Conversion of cyclohexanone oxime (%) | Yield of ε-caprolactam (%) | Selectivity of ε-caprolactam (%) |
|---|---|---|---|
| 1.3 | 100 | 91.5 | 91.5 |
| 2.3 | 100 | 93.2 | 93.2 |
| 3.3 | 100 | 95.0 | 95.0 |
| 4.3 | 100 | 94.5 | 94.5 |
| 5.3 | 100 | 94.5 | 94.5 |
| 6.3 | 100 | 94.5 | 94.5 |
| 7.3 | 100 | 94.7 | 94.7 |
| 9.5 | 100 | 95.0 | 95.0 |
| 11.5 | 100 | 95.1 | 95.1 |
| 13.5 | 100 | 95.0 | 95.0 |
| 15.5 | 100 | 95.2 | 95.2 |
| 18.0 | 100 | 94.7 | 94.7 |
| 20.0 | 99.9 | 94.9 | 95.0 |
| 22.0 | 99.8 | 94.6 | 94.8 |
| 24.0 | 99.8 | 94.8 | 95.0 |
| 25.0 | 99.7 | 94.6 | 94.9 |
| 27.0 | 99.3 | 94.3 | 95.0 |
| 29.0 | 98.8 | 93.6 | 94.7 |
| 31.0 | 98.2 | 93.3 | 95.0 |

REFERENCE EXAMPLE 1

Rearrangement reaction of cyclohexanone oxime was effected in the same manner as in Example 1 except that H.ZSM-5 prepared in Catalyst Preparation Example 1-1 was used as catalyst. The results are shown in Table 2.

TABLE 2

| Time lapsed (hrs) | Conversion of cyclohexanone oxime (%) | Yield of ε-caprolactam (%) | Selectivity of ε-caprolactam (%) |
|---|---|---|---|
| 1.3 | 100 | 73.4 | 73.4 |
| 2.3 | 100 | 76.7 | 76.7 |
| 3.3 | 100 | 79.7 | 79.7 |
| 4.3 | 100 | 81.0 | 81.0 |
| 5.3 | 100 | 83.9 | 83.9 |
| 6.3 | 100 | 84.2 | 84.2 |
| 8.0 | 100 | 86.6 | 86.6 |
| 10.0 | 100 | 87.2 | 87.2 |
| 12.0 | 100 | 86.1 | 86.1 |
| 14.0 | 100 | 88.8 | 88.8 |
| 15.0 | 100 | 90.5 | 90.5 |
| 17.0 | 100 | 91.0 | 91.0 |
| 19.0 | 99.5 | 89.2 | 89.6 |
| 20.0 | 99.3 | 90.1 | 90.7 |
| 25.0 | 97.3 | 92.4 | 89.8 |
| 27.0 | 95.8 | 85.6 | 89.4 |

CATALYST PREPARATION EXAMPLE 2

(2-1) Synthesis of H.ZSM-5

Hydrothermal synthesis and after-treatments were effected in the same manner as in Catalyst Preparation Example 1 except that aqueous aluminum sulfate solution was not used in (1-1).

Thus obtained product was dried at 120° C. for 16 hours. BET surface area of the crystal at this stage was measured by nitrogen gas adsorption method to obtain 11.7 m²/g of external surface area.

This dried crystal was further calcined in air stream at 500°–530° C. for 4 hours to obtain 25 g of powdery white crystal. This was identified to be ZSM-5 by powder X-ray diffraction thereof. Si/Al atomic ratio was 27,000 according to atomic absorption spectroscopy assay.

Thereafter, the crystal was subjected to NH$_4$Cl ion exchange and calcination in accordance with Catalyst Preparation Example 1-1 to obtain H.ZSM-5 crystal. 4MQ adsorption amount of this H.ZSM-5 at 350° C. was nearly 0. Surface acidity was such that it slightly colored with an indicator (dicinnamalacetone) of pKa = −3.0.

(2-2) Surface treatment with TMCS

H.ZSM-5 obtained in Catalyst Preparation Example 2-1 was surface-treated with TMCS in accordance with Catalyst Preparation Example 1-2. Surface acidity of thus treated H.ZSM-5 was pKa = +3.3 measured by indicator method. Amount of acid on the external surface was nearly 0 on the basis of 4MQ adsorption amount at 350° C.

EXAMPLE 2

Rearrangement reaction of cyclohexanone oxime was effected in the same manner as in Example 1 except that TMCS-treated H.ZSM-5 obtained in Catalyst Preparation Example 2-2 was used as a catalyst. The results obtained are shown in Table 3.

TABLE 3

| Time lapsed (hrs) | Conversion of cyclohexanone oxime (%) | Yield of ε-caprolactam (%) | Selectivity of ε-caprolactam (%) |
|---|---|---|---|
| 1 | 100 | 94.6 | 94.6 |
| 2 | 100 | 94.5 | 94.5 |
| 3 | 100 | 95.0 | 95.0 |
| 4 | 100 | 94.9 | 94.9 |
| 5 | 100 | 94.8 | 94.8 |
| 7 | 100 | 95.5 | 95.5 |
| 9 | 100 | 96.3 | 96.3 |
| 12 | 100 | 96.0 | 96.0 |
| 14 | 100 | 95.0 | 95.0 |
| 16 | 100 | 95.1 | 95.1 |
| 18 | 100 | 94.8 | 94.8 |
| 20 | 100 | 94.9 | 94.9 |
| 22 | 100 | 94.8 | 94.8 |
| 24 | 99.7 | 94.7 | 95.0 |
| 26 | 99.7 | 93.7 | 94.0 |
| 28 | 99.4 | 94.3 | 94.9 |
| 30 | 99.2 | 93.9 | 94.7 |
| 32 | 99.2 | 94.8 | 95.6 |
| 34 | 98.9 | 93.9 | 95.0 |
| 35 | 98.6 | 93.8 | 95.1 |

EXAMPLE 3

(Test under high WHSV)

0.3 g (0.5 ml) of the TMCS-treated H.ZSM-5 of 24–48 meshes prepared in Catalyst Preparation Example 2-2 was packed in a quartz glass reaction tube of 32 cm long and 1 cm inner diameter and preheated in N$_2$ stream at 350° C. for 1 hour. Then, 8 wt% cyclohexanone oxime/benzene solution was fed thereto at WHSV = 38.5 hr$^{-1}$ through a vaporizer to carry out reaction. Temperature of the catalyst bed was 350° C. Reaction product was trapped and collected under water cooling and analyzed by gas chromatography. The results obtained are shown in Table 4.

TABLE 4

| Time lapsed (hrs) | Conversion of cyclohexanone oxime (%) | Yield of ε-caprolactam (%) | Selectivity of ε-caprolactam (%) |
| --- | --- | --- | --- |
| 1.3 | 99.3 | 88.3 | 88.9 |
| 2.3 | 98.9 | 90.4 | 91.4 |
| 3.3 | 98.4 | 89.7 | 91.2 |
| 4.3 | 97.7 | 89.6 | 91.8 |
| 5.3 | 97.1 | 87.9 | 90.5 |
| 6.3 | 96.3 | 87.8 | 91.2 |
| 7.3 | 95.5 | 88.9 | 93.1 |

REFERENCE EXAMPLE 2

Rearrangement reaction of cyclohexanone oxime was effected in the same manner as in Example 3 except that the H.ZSM-5 obtained in Catalyst Preparation Example 2-1 was used as a catalyst. The results are shown in Table 5.

TABLE 5

| Time lapsed (hrs) | Conversion of cyclohexanone oxime (%) | Yield of ε-caprolactam (%) | Selectivity of ε-caprolactam (%) |
| --- | --- | --- | --- |
| 1.3 | 100 | 81.1 | 81.1 |
| 2.3 | 100 | 85.5 | 85.5 |
| 3.3 | 99.6 | 85.5 | 85.9 |
| 4.3 | 99.2 | 86.0 | 86.7 |
| 5.3 | 98.7 | 85.7 | 86.9 |
| 6.3 | 98.0 | 83.8 | 85.5 |
| 7.3 | 97.1 | 85.3 | 87.9 |

CATALYST PREPARATION EXAMPLE 3

(3-1) Synthesis of H.ZSM-5

H.ZSM-5 was obtained by hydrothermal synthesis and subsequent after-treatments in the same manner as in Catalyst Preparation Example 2-1 except that ethanol solvent was replaced by ethylene glycol solvent. Analytical values thereof are as follows: Si/Al atomic ratio=26,400, external surface area=8.9 m$^2$/g, acid amount on external surface=2.18 μeq./g and surface acidity pKa=−3.0.

(3-2) Surface treatment with TMCS

H.ZSM-5 obtained in Catalyst Preparation Example 3-1 was surface-treated with TMCS in accordance with Catalyst Preparation Example 1-2. Thus TMCS-treated H.ZSM-5 had a surface acidity of pKa=+3.3 and acid amount on external surface was nearly 0 measured from 4MQ adsorption amount of 350° C.

EXAMPLE 4

(Test under high WHSV)

Rearrangement reaction was effected in the same manner as in Example 3 except that the surface-treated H.ZSM-5 obtained in Catalyst Preparation Example 3-2 was used as a catalyst. The results obtained are shown in Table 6.

TABLE 6

| Time lapsed (hrs) | Conversion of cyclohexanone oxime (%) | Yield of ε-caprolactam (%) | Selectivity of ε-caprolactam (%) |
| --- | --- | --- | --- |
| 1.3 | 99.1 | 85.8 | 86.6 |
| 2.3 | 98.0 | 87.7 | 89.5 |
| 3.3 | 97.5 | 87.9 | 90.2 |
| 4.3 | 97.0 | 88.3 | 91.1 |
| 5.3 | 96.9 | 88.0 | 90.9 |
| 6.3 | 96.3 | 88.2 | 91.6 |
| 7.3 | 95.5 | 86.4 | 90.5 |

REFERENCE EXAMPLE 3

Rearrangement reaction of cyclohexanone oxime was effected in the same manner as in Example 3 except that H.ZSM-5 obtained in Catalyst Preparation Example 3-1 was used as a catalyst. The results are shown in Table 7.

TABLE 7

| Time lapsed (hrs) | Conversion of cyclohexanone oxime (%) | Yield of ε-caprolactam (%) | Selectivity of ε-caprolactam (%) |
| --- | --- | --- | --- |
| 1.3 | 99.5 | 80.3 | 80.7 |
| 2.3 | 97.5 | 79.9 | 81.9 |
| 3.3 | 94.1 | 76.9 | 81.7 |
| 4.3 | 89.8 | 73.9 | 82.3 |
| 5.3 | 86.2 | 70.0 | 81.3 |
| 6.3 | 82.5 | 67.2 | 81.4 |

CATALYST PREPARATION EXAMPLE 4

(4-1) Synthesis of H.ZSM-5

First, solutions having the following compositions were prepared.

| | |
| --- | --- |
| Solution A | |
| Distilled water | 162 g |
| H$_2$SO$_4$ | 16.7 g |
| Al$_2$(SO$_4$)$_3$.17H$_2$O | 0.16 g |
| (n-Pr)$_4$NBr | 20.3 g |
| Solution B | |
| Distilled water | 119.7 g |
| Sodium silicate (JIS No. 3) | 186.3 g |
| Solution C | |
| Distilled water | 281.7 g |
| NaCl | 70.9 g |

Solution A and solution B were simultaneously added dropwise to solution C and they were mixed. The mixture was vigorously stirred with keeping pH of the system at 9–11 (with addition of about 6 g of 48% aqueous NaOH solution to adjust the pH). PH at the completion of mixing was 9.6. The mixture was charged in an autoclave (one l) made of SUS and hydrothermal synthesis was effected with stirring at 400 r.p.m. or more and at 160° C. for 20 hours. The product was cooled and then filtered off, then sufficiently washed with a large amount (up to 7 l) of distilled water until no Cl⁻ ion was detected and further filtered off. The product was dried at 120° C. for 16 hours. BET surface area of the crystal at this stage was measured to obtain 18.3 m$^2$/g of external surface area. Then, thus dried crystal was calcined in air stream at 500°–550° C. for 4 hours to obtain 48 g of a white powdery crystal, which was determined to ZSM-5 according to X-ray diffraction.

To 10 g of this crystal was added 100 g of 5% aqueous NH$_4$Cl solution to carry out ion exchange treatment at 50°–60° C. for one hour, followed by filtration. This ion exchange treatment was repeated four times in total and then washed with distilled water until no Cl⁻ ion was detected and dried at 120° C. for 16 hours. Thus obtained crystal of NH$_4$-form was shaped into particles of 24–48 meshes and then calcined at 500° C. for 4 hours to convert it to ZSM-5 of H-form. This H.ZSM-5 had a surface acidity of pKa=−3 measured by indicator method. 4MQ adsorption amount at 350° C. was 3.62 μeq./g. Si/Al atomic ratio was 550 by atomic absorption spectroscopy assay.

(4-2) Surface treatment with TMCS

H.ZSM-5 obtained in the above (4-1) was subjected to surface treatment with TMCS in accordance with Catalyst Preparation Example 1-2. Surface acidity of thus treated H.ZSM-5 was pKa=−3.0.

EXAMPLE 5

(Test under high WHSV)

Rearrangement reaction of cyclohexanone oxime was carried out in accordance with Example 3 using the surface-treated H.ZSM-5 obtained in the above (4-2). The results obtained are shown in Table 8.

TABLE 8

| Time lapsed (hrs) | Conversion of cyclohexanone oxime (%) | Yield of ε-caprolactam (%) | Selectivity of ε-caprolactam (%) |
|---|---|---|---|
| 1.3 | 97.6 | 84.6 | 86.6 |
| 2.3 | 94.3 | 83.4 | 88.4 |
| 3.3 | 91.3 | 83.2 | 91.1 |
| 4.3 | 90.8 | 82.6 | 91.0 |
| 5.3 | 89.9 | 82.0 | 91.2 |
| 6.3 | 89.8 | 81.4 | 90.6 |

REFERENCE EXAMPLE 4

Rearrangement reaction of cyclohexanone oxime was effected in accordance with Example 3 using H.ZSM-5 of 24–48 meshes prepared in Catalyst Preparation Example 4-1. The results obtained are shown in Table 9.

TABLE 9

| Time lapsed (hrs) | Conversion of cyclohexanone oxime (%) | Yield of ε-caprolactam (%) | Selectivity of ε-caprolactam (%) |
|---|---|---|---|
| 1.3 | 100 | 76.8 | 76.8 |
| 2.3 | 99.3 | 81.0 | 81.6 |
| 3.3 | 98.3 | 79.6 | 81.0 |
| 4.3 | 96.9 | 82.2 | 84.8 |
| 5.3 | 95.4 | 81.0 | 85.0 |
| 6.3 | 93.6 | 79.7 | 85.1 |

COMPARATIVE EXAMPLES 1–3

(Tests under high WHSV)

Reactions were effected in the same manner as in Example 3 except that H.ZSM-5 of 7.9–49.2 in Si/Al atomic ratio was used as catalyst. The results obtained are shown in Tables 10–12.

TABLE 10

| | H.ZSM-5 catalyst (Si/Al = 7.9) | | |
|---|---|---|---|
| Time lapsed (hrs) | Conversion of cyclohexanone oxime (%) | Yield of ε-caprolactam (%) | Selectivity of ε-caprolactam (%) |
| 1.3 | 60.0 | 26.3 | 43.8 |
| 2.3 | 37.3 | 14.5 | 38.9 |
| 3.3 | 30.5 | 10.1 | 33.1 |

TABLE 11

| | H.ZSM-5 catalyst (Si/Al = 17.3) | | |
|---|---|---|---|
| Time lapsed (hrs) | Conversion of cyclohexanone oxime (%) | Yield of ε-caprolactam (%) | Selectivity of ε-caprolactam (%) |
| 1.3 | 66.0 | 24.4 | 37.0 |
| 2.3 | 25.8 | 10.1 | 39.1 |
| 3.3 | 8.9 | 4.1 | 46.0 |

TABLE 12

| | H.ZSM-5 catalyst (Si/Al = 49.2) | | |
|---|---|---|---|
| Time lapsed (hrs) | Conversion of cyclohexanone oxime (%) | Yield of ε-caprolactam (%) | Selectivity of ε-caprolactam (%) |
| 1.3 | 68.5 | 34.3 | 50.1 |
| 2.3 | 24.1 | 13.2 | 53.4 |
| 3.3 | 14.3 | 7.7 | 53.8 |

COMPARATIVE EXAMPLE 4

Reaction was effected in the same manner as in Example 1 except that H.ZSM-5 of Si/Al atomic ratio=49.2 was used as catalyst and 8 wt% cyclohexanone oxime/benzene solution was fed at WHSV=10.8 hr$^{-1}$. The results obtained are shown in Table 13.

TABLE 13

| Time lapsed (hrs) | Conversion of cyclohexanone oxime (%) | Yield of ε-caprolactam (%) | Selectivity of ε-caprolactam (%) |
|---|---|---|---|
| 1.3 | 80.5 | 42.7 | 53.0 |
| 2.3 | 75.0 | 43.6 | 58.2 |
| 3.3 | 68.7 | 42.0 | 61.1 |
| 4.3 | 62.5 | 40.0 | 64.0 |
| 5.3 | 55.2 | 36.2 | 65.5 |
| 6.3 | 47.3 | 31.1 | 65.7 |

COMPARATIVE EXAMPLE 5

Reaction was effected in the same manner as in Example 1 except that 0.6 g of a silica alumina catalyst (manufactured by Shokubai Kasei Co. and alumina content=26%) and 7.53 wt% of cyclohexanone oxime/benzene solution was fed at WHSV=9.77 hr$^{-1}$. The results obtained are shown in Table 14.

TABLE 14

| Time lapsed (hrs) | Conversion of cyclohexanone oxime (%) | Yield of ε-caprolactam (%) | Selectivity of ε-caprolactam (%) |
|---|---|---|---|
| 2 | 100 | 56.1 | 56.1 |
| 3 | 100 | 58.9 | 58.9 |
| 4 | 100 | 57.5 | 57.5 |
| 5 | 100 | 58.9 | 58.9 |
| 6 | 100 | 61.0 | 61.0 |
| 7 | 100 | 61.6 | 61.6 |
| 8 | 100 | 61.3 | 61.3 |
| 9 | 100 | 64.2 | 64.2 |
| 10 | 100 | 61.6 | 61.6 |
| 11 | 100 | 65.1 | 65.1 |
| 12 | 100 | 64.8 | 64.8 |

COMPARATIVE EXAMPLE 6

Reaction was effected in the same manner as in Comparative Example 5 except that 0.6 g of 30 wt% $B_2O_3$/ZnO was used. The results obtained are shown in Table 15.

TABLE 15

| Time lapsed (hrs) | Conversion of cyclohexanone oxime (%) | Yield of ε-caprolactam (%) | Selectivity of ε-caprolactam (%) |
|---|---|---|---|
| 2 | 100 | 98.0 | 98.0 |
| 3 | 97.5 | 92.8 | 95.2 |
| 4 | 95.1 | 85.9 | 90.3 |
| 5 | 92.0 | 81.4 | 88.5 |
| 6 | 88.4 | 76.9 | 87.0 |
| 7 | 81.7 | 67.5 | 82.6 |
| 8 | 74.3 | 59.0 | 79.4 |
| 9 | 65.9 | 49.6 | 75.3 |
| 10 | 54.1 | 39.2 | 72.5 |
| 11 | 47.6 | 31.4 | 66.0 |
| 12 | 35.2 | 20.8 | 59.3 |

CATALYST PREPARATION EXAMPLE 5

H.ZSM-5 of Si/Al atomic ratio=6,400 was prepared in accordance with Catalyst Preparation Example 1-1. Surface acidity of the product was Ho=−3 measured by indicator method. 4MQ adsorption amount at 350° C. was 0.8 μeq./g and external surface area was 29.2 m²/g.

0.5 g of thus obtained H.ZSM-5 of 24–48 meshes was subjected to surface treatment in accordance with Catalyst Preparation Example 1-2 at 350° C. for 5 hours with flowing dichlorodimethylsilane or chlorotrimethylgermanium at 1.18 mmol/hr and N₂ gas at 1 l/hr.

EXAMPLES 6 AND 7

(Tests under high WHSV)

Rearrangement reaction of cyclohexanone oxime was effected in accordance with Example 3 using the surface-treated H.ZSM-5 obtained in Catalyst Preparation Example 5. The results obtained are shown in Tables 16 and 17.

REFERENCE EXAMPLE 5

Rearrangement reaction was effected in accordance with Example 3 using untreated H.ZSM-5 obtained in the first part of Catalyst Preparation Example 5. The results obtained are shown in Table 18.

TABLE 16

Results of reaction using Me₂SiCl₂ treated H.ZSM-5 catalyst

| Time lapsed (hrs) | Conversion of cyclohexanone oxime (%) | Yield of ε-caprolactam (%) | Selectivity of ε-caprolactam (%) |
|---|---|---|---|
| 1.3 | 97.5 | 87.2 | 89.4 |
| 2.3 | 94.9 | 88.6 | 93.4 |
| 3.3 | 91.6 | 86.2 | 94.1 |
| 4.3 | 91.2 | 85.7 | 94.0 |
| 5.3 | 88.8 | 83.2 | 93.7 |
| 6.3 | 87.5 | 81.8 | 93.5 |

TABLE 1

Results of reaction using Me₃GeCl treated H.ZSM-5 catalyst

| Time lapsed (hrs) | Conversion of cyclohexanone oxime (%) | Yield of ε-caprolactam (%) | Selectivity of ε-caprolactam (%) |
|---|---|---|---|
| 1.3 | 98.9 | 90.8 | 91.8 |
| 2.3 | 98.0 | 89.9 | 91.7 |
| 3.3 | 96.1 | 88.5 | 92.1 |
| 4.3 | 96.0 | 89.7 | 93.4 |
| 5.3 | 95.5 | 88.5 | 92.7 |
| 6.3 | 94.4 | 86.5 | 91.6 |

TABLE 18

Results of reaction using untreated H.ZSM-5 catalyst

| Time lapsed (hrs) | Conversion of cyclohexanone oxime (%) | Yield of ε-caprolactam (%) | Selectivity of ε-caprolactam (%) |
|---|---|---|---|
| 1.3 | 100 | 83.8 | 83.8 |
| 2.3 | 100 | 85.8 | 85.8 |
| 3.3 | 99.7 | 85.4 | 85.7 |
| 4.3 | 99.4 | 86.5 | 87.1 |
| 5.3 | 99.1 | 85.3 | 86.1 |
| 6.3 | 98.6 | 86.1 | 87.3 |

CATALYST PREPARATION EXAMPLE 6

(6-1) Synthesis of borosilicate zeolite

In a 1.5 l stainless steel autoclave were charged 217.5 g of 10% aqueous tetra-n-propylammonium hydroxide solution, 214 g of ethanol, 2 ml of an aqueous solution containing 14.8 mg of boric acid and 100 g of high purity tetraethylorthosilicate (Al<10 ppm) in this order and were well stirred for one hour. This mixed liquid had a pH of about 12.5. This autoclave was closed and hydrothermal synthesis was effected for 48 hours with stirring at 400 r.p.m. or more and keeping the inner temperature at 105° C. Pressure within the autoclave reached about 2.5 Kg/cm².

After completion of the hydrothermal synthesis, the product was subjected to filtration, washing and drying in accordance with the procedure of latter part of Catalyst Preparation Example 1. BET surface area of the product was measured to obtain 15.0 m²/g as external surface area. This dried crystal was further calcined in air stream at 500°–550° C. for 4 hours to obtain 29.0 g of a powdery white crystal. This was identified to be a borosilicate having the structure similar to that of ZSM-5 according to powder X-ray diffraction. Si/B atomic ratio thereof was 3,020 according to atomic absorption spectroscopy assay. This was converted to borosilicate of H-form by subjecting to NH₄Cl ion exchange, washing and calcination. Surface acidity thereof was Ho=−3.0 according to indicator method and amount of acid on external surface was 1.08 μeq./g calculated from 4MQ adsorption amount.

(6-2) Surface treatment 0.5 g of thus obtained borosilicate was surface treated in accordance with Catalyst Preparation Example 1-2 at 350° C. for 5 hours with flowing TMCS at 1.18 mmol/hr and N₂ gas at 1 l/hr.

EXAMPLE 8

(Test under high WHSV)

Rearrangement reaction of cyclohexanone oxime was effected in accordance with Example 3 using the TMCS treated borosilicate obtained in Catalyst Preparation Example 6-2 as catalyst. The results obtained are shown in Table 19.

TABLE 19

| Time lapsed (hrs) | Conversion of cyclohexanone oxime (%) | Yield of ε-caprolactam (%) | Selectivity of ε-caprolactam (%) |
|---|---|---|---|
| 1.3 | 100 | 90.3 | 90.3 |
| 2.3 | 99.5 | 90.9 | 91.4 |
| 3.3 | 99.2 | 91.4 | 92.1 |
| 4.3 | 98.6 | 90.8 | 92.2 |
| 5.3 | 97.9 | 90.3 | 91.0 |

TABLE 19-continued

| Time lapsed (hrs) | Conversion of cyclohexanone oxime (%) | Yield of ε-caprolactam (%) | Selectivity of ε-caprolactam (%) |
|---|---|---|---|
| 6.3 | 97.5 | 88.3 | 90.6 |

REFERENCE EXAMPLE 6

Rearrangement reaction of cyclohexanone oxime was effected in accordance with Example 3 using the borosilicate of H-form prepared in Catalyst Preparation Example 6-1 as catalyst. The results obtained are shown in Table 20.

TABLE 20

| Time lapsed (hrs) | Conversion of cyclohexanone oxime (%) | Yield of ε-caprolactam (%) | Selectivity of ε-caprolactam (%) |
|---|---|---|---|
| 1.3 | 100 | 74.3 | 74.3 |
| 2.3 | 99.7 | 84.9 | 85.2 |
| 3.3 | 99.3 | 85.7 | 86.3 |
| 4.3 | 98.8 | 81.3 | 82.3 |
| 5.3 | 97.9 | 83.0 | 84.8 |
| 6.3 | 97.0 | 82.9 | 85.5 |

CATALYST PREPARATION EXAMPLE 7

0.5 g of the borosilicate obtained in Catalyst Preparation Example 6-1 was subjected to surface-treatment in accordance with Catalyst Preparation Example 1-2 at 350° C. for 5 hours with flowing dimethoxydimethylsilane at 1.18 mmol/hr and $N_2$ gas at 1 l/hr.

EXAMPLE 9

(Test under high WHSV)

Rearrangement reaction of cyclohexanone oxime was effected in accordance with Example 3 using the borosilicate treated with $Me_2Si(OMe)_2$ which was obtained in Catalyst Preparation Example 7 as catalyst. The results obtained are shown in Table 21.

TABLE 21

| Time lapsed (hrs) | Conversion of cyclohexanone oxime (%) | Yield of ε-caprolactam (%) | Selectivity of ε-caprolactam (%) |
|---|---|---|---|
| 1.3 | 95.6 | 85.0 | 88.9 |
| 2.3 | 91.3 | 84.5 | 92.5 |
| 3.3 | 88.0 | 81.0 | 92.1 |
| 4.3 | 84.1 | 79.8 | 94.9 |
| 5.3 | 82.2 | 76.3 | 92.8 |
| 6.3 | 80.1 | 72.2 | 90.1 |

CATALYST PREPARATION EXAMPLE 8

A gallosilicate of H form having Si/Ga atomic ratio=1,986 was synthesized in accordance with Catalyst Preparation Example 6-1. Acidity thereof was Ho=+3.0 measured by indicator method, external surface area was 16.9 m²/g and amount of acid on external surface was 4.5 μeq./g. Thus obtained H-form gallosilicate was surface-treated in accordance with Catalyst Preparation Example 1-2 at 350° C. for 5 hours with flowing 1.18 mmol/hr of TMCS and 1 l/hr of $N_2$ gas.

EXAMPLE 10

(Test under high WHSV)

Rearrangement reaction of cyclohexanone oxime was effected in accordance with Example 3 using the TMCS-treated gallosilicate obtained in Catalyst Preparation Example 8 as catalyst. The results obtained are shown in Table 22.

REFERENCE EXAMPLE 8

Rearrangement reaction of cyclohexanone oxime was effected in accordance with Example 3 using untreated H-form gallosilicate obtained in the first part of Catalyst Preparation Example 8 as catalyst. The results obtained are shown in Table 23.

TABLE 22

| Time lapsed (hrs) | Conversion of cyclohexanone oxime (%) | Yield of ε-caprolactam (%) | Selectivity of ε-caprolactam (%) |
|---|---|---|---|
| 1.3 | 98.7 | 89.2 | 90.4 |
| 2.3 | 96.1 | 87.3 | 90.8 |
| 3.3 | 94.1 | 83.9 | 89.2 |
| 4.3 | 91.7 | 82.2 | 89.7 |
| 5.3 | 89.5 | 80.7 | 90.2 |
| 6.3 | 87.4 | 79.5 | 91.0 |

TABLE 23

| Time lapsed (hrs) | Conversion of cyclohexanone oxime (%) | Yield of ε-caprolactam (%) | Selectivity of ε-caprolactam (%) |
|---|---|---|---|
| 1.3 | 99.7 | 81.6 | 81.9 |
| 2.3 | 99.2 | 81.4 | 82.1 |
| 3.3 | 98.4 | 82.1 | 83.5 |
| 4.3 | 97.4 | 82.5 | 84.7 |
| 5.3 | 95.9 | 84.2 | 87.8 |
| 6.3 | 95.0 | 79.9 | 84.2 |

We claim:

1. A method for preparing ε-caprolactam which comprises bringing cyclohexanone oxime in a gaseous phase into contact with a crystalline zeolite catalyst having a constraint index of 1–12 which has been surface treated with an organometallic compound represented by the following general formula (I):

$$R_{4-n}MX_n \quad (I)$$

wherein R which may be identical or different represent an alkyl group of 1–6 carbon atoms or phenyl group, M represents Si or Ge, X represents Cl or an alkoxy group of 1–6 carbon atoms and n represents 1 or 2.

2. A method for preparing ε-caprolactam according to claim 1 wherein the crystalline zeolite catalyst is an alumino-silicate zeolite having a Si/Al atomic ratio of at least 500.

3. A method for preparing ε-caprolactam according to claim 1 wherein the crystalline zeolite catalyst is a metallo-silicate catalyst having a Si/metal atomic ratio of at least 500.

4. A method for preparing ε-caprolactam according to claim 1 wherein the crystalline zeolite catalyst has an external surface area of at least 5 m²/g.

5. A method for preparing ε-caprolactam according to claim 1 wherein cyclohexanone oxime is diluted with benzene or toluene.

6. A method for preparing ε-caprolactam according to claim 1 wherein cyclohexanone oxime is fed at WHSV of 1–50 hr⁻¹.

7. A method for preparing ε-caprolactam according to claim 6 wherein cyclohexanone oxime is fed at WHSV of 5–10 hr⁻¹.

8. A method for preparing ε-caprolactam according to claim 1 wherein cyclohexanone oxime is fed with an inert gas as a carrier gas.

9. A method for preparing ε-caprolactam according to claim 1 wherein the contact is made at a temperature of 300°–450° C.

* * * * *